United States Patent
Gouse

(10) Patent No.: US 11,045,410 B2
(45) Date of Patent: Jun. 29, 2021

(54) NAIL POLISH DIP SYSTEM

(71) Applicant: MYCONE DENTAL SUPPLY cO., iNC., Gibbstown, NJ (US)

(72) Inventor: Kendra Gouse, Philadelphia, PA (US)

(73) Assignee: Mycone Dental Supply Co., Inc., Gibbstown, NJ (US)

( * ) Notice: Subject to any disclaimer, the term of this patent is extended or adjusted under 35 U.S.C. 154(b) by 0 days.

(21) Appl. No.: 16/045,827

(22) Filed: Jul. 26, 2018

(65) Prior Publication Data

US 2020/0030216 A1   Jan. 30, 2020

(51) Int. Cl.
  *A61K 8/55*   (2006.01)
  *A61Q 3/02*   (2006.01)
  *A61K 8/81*   (2006.01)

(52) U.S. Cl.
  CPC .............. *A61K 8/55* (2013.01); *A61K 8/8152* (2013.01); *A61Q 3/02* (2013.01)

(58) Field of Classification Search
  CPC ........... A61K 8/55; A61K 8/8152; A61Q 3/02
  See application file for complete search history.

(56) References Cited

U.S. PATENT DOCUMENTS

| | | | | |
|---|---|---|---|---|
| 3,928,113 | A | * | 12/1975 | Rosenberg ............... A61K 8/87 132/73 |
| 5,770,184 | A | * | 6/1998 | Keller .................. A61K 8/8123 424/401 |
| 6,547,917 | B1 | | 4/2003 | Misiak et al. |
| 8,747,819 | B1 | | 6/2014 | Doan |
| 9,597,272 | B2 | | 3/2017 | Li et al. |

OTHER PUBLICATIONS

Kiara Sky, Dip Powder—D467 Chocolate Glaze, publication date (via Wayback Machine): Apr. 28, 2017. (Year: 2017).*
J. P. Cronin, D. C. Pepper, Zwitterionic polymerization of butyl cyanoacrylate by triphenylphosphine and pyridine, Macromolecular Chem. & Phys., Jan. 1988, 85-102, 189(1).

* cited by examiner

*Primary Examiner* — Genevieve S Alley

(57) ABSTRACT

A powder composition for forming a cosmetic nail coating comprises an acrylic polymer or copolymer, and about 0.01 wt % to about 1.0 wt % of tertiary phosphine. The tertiary phosphine comprises three aryl groups, alkyl groups, or combination thereof. An example of the tertiary phosphine is a triaryl phosphine that may be substituted with 1 to 3 alkyl groups. A method of forming a cosmetic nail coating comprises the steps of (i) applying to a nail a cyanoacrylate adhesive; and (ii) contacting the nail with the powder composition. No application of an activator is necessary. The advantages of such a method include that fewer steps are needed in order to obtain a nail coating, the increased speed that the system cures, and a safer toxicological profile of the ingredients.

21 Claims, No Drawings

ND POLISH DIP SYSTEM

NAIL POLISH DIP SYSTEM

FIELD OF THE INVENTION

The present invention is directed generally to the field of nail manicuring. More specifically, this invention applies to nail care products and processes for treating nails.

DESCRIPTION OF RELATED TECHNOLOGY

The traditional dipping powder system comprises three components: a liquid cyanoacrylate resin, a polymer dipping powder, and an activator. The manicurist using the traditional dipping powder system coats a single nail with the resin, then immediately dips the same nail at a 45-degree angle into a dipping powder. Any excess powder is tapped off, and this process is repeated on the other four nails of the same hand. When the nails are dry to the touch, a sanitized cosmetic brush is used to wipe off any remaining loose powder. A second layer of the resin is then used, and the dipping of each finger into the same or different powder is repeated. Any remaining loose powder is then brushed off. The above steps are then followed by an application of an activator to all five nails, making sure that the entire surface of the nail is covered. The activator layer is allowed to dry completely. The activator comprises a solvent, such as ethyl acetate, butyl acetate, isopropyl acetate, or a mixture thereof, and a tertiary amine.

There are several problems with the use of the traditional dipping powder. Firstly, the traditional dipping system contains too many steps. Secondly, the traditional dipping system takes too much time. Thirdly, the traditional dipping system is prone to yellowing due to the use of amine activators.

A nail composition is taught in U.S. Pat. No. 9,597,272. The invention relates to nail composition sets comprising at least one primer, at least one bonding composition, and at least one color coat, wherein the primer comprises water and at least one adhesive compound and preferably further comprises at least one water-soluble film-forming agent and/or at least one plasticizer.

A nail enamel composition, method of preparation and method of use are disclosed in U.S. Pat. No. 8,747,819. A nail enamel composition has a film-forming mixture in a compatible solvent. The film-forming mixture includes nitrocellulose as a major component. The composition further includes a cyanoacrylate mixture comprising cyanoacrylate and a free radical inhibitor, the cyanoacrylate mixture being substantially free of toluene. The disclosure includes a method of preparation of the composition and a method of use of the composition.

Zwitterionic polymerization of butyl cyanoacrylate by triphenylphosphine and pyridine is discussed in J. P. Cronin, D. C. Pepper Macromol. Chem. & Phys. January 1988. This reference describes a re-examination of the kinetics and molecular weights formed in the zwitterionic polymerization of butyl cyanoacrylate by triphenylphosphine ($Ph_3P$) and pyridine (Py) in THF, and an extension to include the solvents, diethyl ether ($Et_2O$), dimethoxyethane (DME) and hexane. In THF, the previously observed kinetics were confirmed, yielding evidence for absence of termination, and values for rate constants for initiation (ki) and propagation ($k_p$) with substantial agreement between the values for $K_p$ obtained from both systems. At 20° C., the mean value found for $k_p$ in THF was $3 \times 10^5$ L·mol$^{-1}$ s$^{-1}$; in $Et_2O$, some 10 times lower, and in hexane, 10 times lower again. The temperature dependence of $k_p$ in THF was confirmed to be extremely low and anomalous; in $Et_2O$ rather greater and near-normal, corresponding to an energy of activation of ca. 5 kcal mol$^{-1}$. A correction procedure enabled the large experimental scatter in the $k_p$ values to be reduced sufficiently to reveal trends downwards at higher concentrations of propagating species, i.e. evidence for their dissociation on dilution. In Py-initiated polymerizations, excess of pyridinium salts did not depress $k_p$; evidence that the propagating species are preponderately paired ions, not free. It was concluded that at 20° C. these species are mainly 'tight' ion-pairs in all solvents, and remain so in $Et_2O$ at all temperatures down to −80° C. In THF, over this temperature range, there is increasing solvation producing an increasing proportion of more reactive 'solvent-separated' ion-pairs. The molecular weights produced under all conditions were high (Mn usually 1 to $3 \times 10^6$). Those produced by high concentration of $Ph_3P$ did not conform to theory; others followed the 'no-termination' theory as modified to allow for a small effect of transfer.

Activator for cyanoacrylate adhesives are taught in U.S. Pat. No. 6,547,917. Organic compounds containing the structural element —N=C—S—S—C=N— are suitable in dilute solution as activators for the accelerated hardening of cyanoacrylate adhesives. As compared with the known accelerators, they have the following advantage: good accelerating action, but they nevertheless permit a long waiting time between application of the activator and application of the adhesive. In addition, they avoid spontaneous, merely superficial hardening.

A nail enamel composition, method of preparation and method of use are discussed in U.S. Pat. No. 8,747,819. A nail enamel composition has a film-forming mixture in a compatible solvent. The film-forming mixture includes nitrocellulose as a major component. The composition further includes a cyanoacrylate mixture comprising cyanoacrylate and a free radical inhibitor, the cyanoacrylate mixture being substantially free of toluene. The invention includes a method of preparation of the composition, and a method of use of the composition.

Although many advances in the art of formulating acrylic nail system have been made to solve various problems, overcoming problems associated with powder dipping systems remain elusive.

SUMMARY OF THE INVENTION

The present invention relates to a powder composition for forming a cosmetic nail coating comprising: (a) an acrylic polymer or copolymer; and (b) about 0.01 wt % to about 1.0 wt % of tertiary phosphine of formula $PAr_aR_{3-a}$, wherein each Ar is independently selected from the group consisting of $C_6H_5$, $C_6H_{5-n}R'_n$, $C_{10}H_7$, $C_{10}H_{7-n}R'_n$; a=0, 1, 2, or 3; n=0, 1, 2, or 3; each R is independently an alkyl group comprising 0 to 8 carbons; each R' is independently an alkyl group comprising 0 to 8 carbons; and wherein the wt % are with respect to the powder composition.

One of the observed advantages of the method of applying the formulation of the present invention over the prior art dip system is the lower level of gentleness that needs to be exhibited when shaking off or brushing off any excess powder. Another advantage is that fewer steps are needed in order to obtain a nail coating. Yet another advantage is the increased speed that the system cures. Still another advantage of the method of using the formulation of the present invention is the safer toxicological profile.

One of the aspects of the present invention is a powder composition for forming a cosmetic nail coating. The powder is a mixture of at least two components: an acrylic polymer or copolymer, and a tertiary phosphine.

The acrylic polymer or copolymer is similar to the acrylic polymers or copolymers that are present in polymer powders that are used in the nail manicuring industry. Such polymer powders comprise polymers comprising units of formula —[C(H,Me)(C(O)OAk)-CH$_2$]—, wherein Ak is an alkyl group comprising 1 to 8 carbons.

The acrylic powder comprises a Lewis base. Examples of Lewis bases include compounds with a pnicogen, a chalcogen, or a halogen Examples of pnicogen Lewis bases include tertiary amines, tertiary phosphines, tertiary arsines, tertiary stibines, and tertiary bi smuthines.

The powder mixture of the present invention includes an acrylic polymer or a copolymer, and a tertiary phosphine. The tertiary phosphine is a compound comprising a phosphorus atom that is substituted with three substituents, none of which is hydrogen. The tertiary phosphine of the present invention has the formula $PAr_3R_{3-a}$, wherein a=0, 1, 2, or 3. The aromatic group is a single ring with the formula $C_6H_{5-n}R'_n$, or a double ring aromatic group with the formula $C_{10}H_{7-n}R'_n$, wherein R' is an alkyl group comprising 0 to 8 carbons, and n is 0, 1, 2, or 3.

The tertiary phosphine is triaryl phosphine of formula $PAr_3$, wherein each Ar is independently either $C_6H_5$ or $C_6H_{5-n}R'_n$, wherein n=0 to 3. Under one embodiment the triaryl phosphine is triphenylphosphine.

The present invention is also directed to a powder composition for forming a cosmetic nail coating comprising (a) acrylic polymer or copolymer; and (b) about 0.01 wt % to about 1.0 wt % of a tertiary phosphine, wherein the tertiary phosphine comprises more than one phosphine atom, such as 2,2'-bis(diphenylphosphino-1,1'-biphenyl; 4,12-bis(diphenylphosphino)-[2.2]-paracyclophane; 4,12-bis[di(3,5-xylyl)phosphino]-[2.2]-paracyclophane; and 1,4-bis(diphenylphosphino)butane.

The tertiary phosphine or the triaryl phosphine of the present invention not limited by any physical characteristic, as long as the use of the powder composition comprising the tertiary phosphine is easily flowable, and wets out to provide an even coating Under one embodiment the even coating is a porous-free coating.

The powder composition comprising the acrylic polymer or copolymer, and tertiary phosphine have an easy flow. The flow factor ff is more than about 4, or more than about 6, or more than about 8.

The powder composition for forming a cosmetic nail coating comprises polyethyl methacrylate polymer, and about 0.01 wt % to about 1.0 wt % of tertiary phosphine. Under one embodiment the powder of composition comprises about 0.03 wt % to about 0.50 wt % of triphenylphosphine. Under another embodiment, the powder of composition comprises about 0.05 wt % to about 0.25 wt % of triphenylphosphine.

The powder composition for forming a cosmetic nail coating comprises optionally also comprises one or more excipients, such as flow modifiers and colorants.

The powder composition is shelf stable. The powder composition is stable in a dark container at 20° C. for more than six months.

The present invention relates to a method of forming a cosmetic nail coating comprising the steps of (i) applying to a nail a cyanoacrylate adhesive; and (ii) contacting the nail with a powder composition comprising (a) acrylic polymer or copolymer; and (b) about 0.01 wt % to about 1.0 wt % of tertiary phosphine of formula $PAr_aR_{3-a}$, wherein each Ar is independently selected from the group consisting of $C_6H_5$, $C_6H_{5-n}R'_n$, $C_{10}H_7$, $C_{10}H_{7-n}R'_n$; a=0, 1, 2, or 3, n=0, 1, 2, or 3; each R is independently an alkyl group comprising 0 to 8 carbons; each R' is independently an alkyl group comprising 0 to 8 carbons; and wherein wt % is with respect to the powder composition.

This method comprises two steps. In the first step, the manicurist applies a layer of a cyanoacrylate adhesive. Immediately thereafter, the manicurist contacts the nail coated with the layer of the cyanoacrylate adhesive with a powder composition comprising the acrylic polymer or copolymer and tertiary phosphine.

Optionally, after the application of the two steps, an air-dry top coat is added to the nail and allowed to air dry.

Cyanoacrylate adhesives are well known in the nail industry. For example, cyanoacrylate adhesives are used in the traditional dip powder systems. Further, cyanoacrylate adhesives are used to adhere artificial nails to natural nails.

Suitable cyanoacrylates include methyl 2-cyanoacrylate, ethyl 2-cyanoacrylate, n-butyl cyanoacrylate, 2-octyl cyanoacrylate, and a mixture thereof.

The present invention relates to a nail coating composition formed by the above-described method.

The nail coating composition under one embodiment is the layered mixture of cyanoacrylate adhesive and the powder composition. The nail coating composition formed by the method of applying the cyanoacrylate adhesive and powder composition is fully cured without the need for the activator. Specifically, the present invention is directed to a cured nail coating composition formed by (i) applying to a nail a cyanoacrylate adhesive, and (ii) contacting the nail with a powder composition comprising (a) acrylic polymer or copolymer; and (b) about 0.01 wt % to about 1.0 wt % of tertiary phosphine, wherein the cured nail composition is cured only by the reaction of the cyanoacrylate adhesive, the acrylic polymer or copolymer, and the tertiary phosphine.

The cure time may be less than about 1 minute or less than about 40 seconds.

The yellowness index of the cured nail composition of the present invention is less than the yellowness index for the equivalent formulation comprising tertiary amine instead of tertiary phosphine.

DETAILED DESCRIPTION OF THE INVENTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in a certain order, in many instances, these steps may be performed in any order as may be appreciated by one skilled in the art, and the methods are not limited to the particular arrangement of steps disclosed herein.

As used herein and in the appended claims, the singular forms "a", "an", and "the" include plural references unless the context clearly dictates otherwise. The singular form of any class of the ingredients refers not only to one chemical species within that class but also to a mixture of those chemical species; for example, the term "phosphine" in the singular form, may refer to a mixture of compounds each of which is also a phosphine. The terms "a" (or "an"), "one or more" and "at least one" may be used interchangeably herein. It is also to be noted that the terms "comprising", "including", and "having" may be used interchangeably.

The abbreviations and symbols as used herein, unless indicated otherwise, take their ordinary meaning. The term "wt %" means percent by weight.

The term "about" when referring to a number means±10%. For example, the phrase "about 0.01 wt %" refers to a number between and including 0.00900 wt % and 0.0100 wt %. The term "about" refers only to those value ranges that are physically or theoretically possible.

The term "client" refers to a person whose nails are being treated.

The term "manicurist" is a worker skilled or licensed in the art of providing nail extensions, artificial nails, acrylic nails, gel nails, and other manicure services for clients. Alternative names for a manicurist may include nail technician, technician and cosmetologist. Such a person may work for pay at a nail salon, or may be a manicure aficionado.

Under one embodiment of the present invention, the client and the manicurist are two different individuals. Although the description of the invention below describes the manicurist and the client as two separate individuals, it is understood that the claimed invention and methods are also suitable for use by a single person who is both a manicurist and a client. Under another embodiment of the present invention, the client and the manicurist are the same person.

The terms "nail", refer to either a fingernail or a toenail. The term "nail" also refers to a human nail, as well as to any toughened keratin at the end of a digit of a non-human animal. The phrase "cosmetic nail coating" refers to the hardened, fully cured substance covering a part or all of the nail, and any portions of this substance that extends or is built beyond the free edge of the nail.

The abbreviation or term "DHEPT" means N,N-dihydroxyethyl-p-toluidine. The abbreviation or term "TPP" means triphenylphosphine. The abbreviation or term "BPO" means benzoyl peroxide.

The term "mixture" refers to a composition comprising one or several ingredients listed therewith.

When referring to a composition as a compound or a polymer, the composition may be of any purity suitable for the purpose.

Any member in a list of species (such as compounds) that are used to exemplify or define a genus (such as a composition or a class of compounds), may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

The present invention relates to a powder composition for forming a cosmetic nail coating comprising: (a) an acrylic polymer or copolymer; and (b) about 0.01 wt % to about 1.0 wt % of tertiary phosphine of formula $PAr_aR_{3-a}$, wherein each Ar is independently selected from the group consisting of $C_6H_5$, $C_6H_{5-n}R'_n$, $C_{10}H_7$, $C_{10}H_{7-n}R'_n$; a=0, 1, 2, or 3; n=0, 1, 2, or 3; each R is independently an alkyl group comprising 0 to 8 carbons; each R' is independently an alkyl group comprising 0 to 8 carbons; and wherein the wt % are with respect to the powder composition.

One of the observed advantages of the method of applying the formulation of the present invention over the prior art dip system is the lower level of gentleness that needs to be exhibited when shaking off or brushing off any excess powder. When using the prior art dip system, the manicurist needs to be gentle when brushing off excess powder before applying the next coat of resin, otherwise the application of the resin will mar. However, when using the dip system of the present invention, the manicurist does not have to be as gentle. This is advantageous especially for manicurists lacking the skills or training of experienced professional manicurists.

Another advantage of the method of applying the formulation of the present invention over the prior art dip system is the fewer steps that the manicurist needs to take in order to obtain a nail coating. The step of applying the activator is not necessary.

Another advantage of the method of using the formulation of the present invention is the increased speed that the system cures. With the existing nail dip system, the curing time is about 2 minutes and 30 seconds, whereas with the nail dip system of the present invention, the curing time is about 30 to 40 seconds.

Still another advantage of the method of using the formulation of the present invention is the safer toxicological profile. The use of the present formulation obviates the use of tertiary amines, some of which are regulatorily restricted, for example, such as under laws based on California Proposition 65.

One of the aspects of the present invention is a powder composition for forming a cosmetic nail coating. The powder is a mixture of at least two components: an acrylic polymer or copolymer, and a tertiary phosphine.

The powder may optionally contain additional components besides the acrylic polymer or copolymer. These components may be excipients that are added by a formulator, or impurities that occurred during the process to prepare the acrylic polymer or copolymer. An example of an additional component is BPO, benzoyl peroxide.

Under one embodiment of the present invention, the acrylic polymer or copolymer is similar to the acrylic polymers or copolymers that are present in polymer powders that are used in the nail manicuring industry. Such polymer powders comprise polymers comprising units of formula —[C(H,Me)(C(O)OAk)-CH$_2$]—, wherein Ak is an alkyl group comprising 1 to 8 carbons.

Examples of suitable acrylic polymers or copolymers include polymethyl methacrylate, polyethyl methacrylate, polybutyl methacrylate, or copolymers thereof.

Under one embodiment of the present invention, the acrylic polymer or copolymer is a polyethyl methacrylate polymer.

The term "acrylic" as used, for example, in the phrase "acrylic polymer or copolymer", is to be interpreted broadly. Under one embodiment, the term acrylic includes methacrylic, i.e., polymers that comprise the units of formula —[C(Me)(C(O)OAk)-CH$_2$]—, wherein Ak is an alkyl group.

Examples of a suitable polymer comprise poly(methyl methacrylate), poly(ethyl methacrylate), and a mixture thereof. A suitable polymer is poly(methyl methacrylate), or PMMA.

Under one embodiment of the present invention, the acrylic powder comprises a Lewis base. The Lewis base has an available lone electron pair to catalyze the cyanoacrylate polymerization. Examples of Lewis bases include compounds with pnicogens (main group elements of Group 15), chalcogens (main group elements of Group 16), halogens (main group elements of Group 17). Examples of Group 15 elements include nitrogen, phosphorus, arsenic, antimony, and bismuth. Examples of Group 16 elements include oxygen, sulfur, selenium, and tellurium. Examples of Group 17 elements include chlorine, bromine, and iodine.

Under one embodiment of the present invention, the acrylic powder comprises a pnicogen Lewis base. Examples of pnicogen Lewis bases include tertiary amines, tertiary phosphines, tertiary arsines, tertiary stibines, and tertiary bismuthines.

Although these pnicogen Lewis bases may indeed successfully catalyze the cyanoacrylate polymerization, certain pnicogen Lewis bases are preferred over others. For example, tertiary amines, tertiary phosphines, and tertiary bismuthines may be preferred over tertiary arsines or tertiary stibines due to health concerns. Tertiary phosphines may be preferred over tertiary amines due to lower yellowing and faster curing time.

The powder mixture of the present invention includes an acrylic polymer or a copolymer, and a tertiary phosphine. The tertiary phosphine is a compound comprising a phosphorus atom that is substituted with three substituents, none of which is hydrogen.

Under one embodiment, the tertiary phosphine of the present invention has the formula $PAr_3R_{3-a}$, wherein a=0, 1, 2, or 3. The symbol "Ar" is an aryl group, and the symbol "R" is an alkyl group. The tertiary phosphine may have any of the following formulas: $PAr_3$, $PAr_2R$, $PArR_2$, or $PR_3$.

The term "aryl" means aromatic carbocyclic group. Under one embodiment, the aromatic group is a single ring with the formula $C_6H_{5-n}R'_n$, wherein R' is an alkyl group comprising 0 to 8 carbons, and n is 0, 1, 2, or 3. Under another embodiment, the aromatic group is a double ring aromatic group with the formula $C_{10}H_{7-n}R'_n$, wherein R' is an alkyl group comprising 0 to 8 carbons, and n is 0, 1, 2, or 3.

Exemplary aryl includes phenyl, naphthyl, phenyl substituted with one or more aryl group substituents, and naphthyl substituted with one or more aryl group substituents. Under one embodiment the aryl group substituents is an alkyl group comprising 0 to 8 carbons.

Examples of tertiary phosphines of formula $PAr_aR_{3-a}$ include compounds of formula $PR_3$, wherein R is an alkyl group;

Under one embodiment in the formula $PAr_3R_{3-a}$ the variable a is an integer with a value of 0, 1, 2, or 3. Under such embodiment, the tertiary phosphine is a pure compound of a single formula.

Under an alternative embodiment, in the formula $PAr_3R_{3-a}$ the variable a is a number with a value of anywhere from 0 to 3, including non-integer numbers. This is possible when the tertiary phosphine is a mixture of various tertiary phosphines. For example, a mixture of 50% PPh3 and 50% of $PPh_2Bu$ will result in a tertiary phosphine with the formula $PPh_{2.5}Bu_{0.5}$.

The tertiary phosphine group may contain one or more alkyl groups bound to the phosphine atom. The definition of an alkyl group as used herein includes saturated hydrocarbyl groups that are straight chains, branched, and alicyclic. Straight chain alkyl groups include methyl, ethyl, n-propyl, n-pentyl, n-hexyl, n-heptyl, n-octyl, and mixtures thereof. Branched alkyl groups include propyl, pentyl, hexyl, heptyl, octyl, and mixtures thereof, wherein each of the groups is not linear.

An alicyclic group is a hydrocarbyl group that is both aliphatic and cyclic. The alicyclic group is fully saturated, i.e., contains only single bonds. Examples of aliphatic groups include unsubstituted cyclic groups, such as cyclohexyl group, $—C_6H_{11}$. Examples also include cyclic groups that are substituted with alkyl groups, such as methylcyclohexyl group, $—(C_6H_{10})$-Me. Examples also include alkyl groups that are further substituted by a cycloalkyl group, such as cyclohexylethylene group, $—CH_2—CH_2—C_6H_{11}$.

Under one embodiment, the tertiary phosphine is triaryl phosphine of formula $PAr_3$, wherein each Ar is independently either $C_6H_5$ or $C_6H_{5-n}R'_n$, wherein n=0 to 3. $C_6H_5$ is an unsubstituted phenyl group. $C_6H_{5-n}R'_n$ is a phenyl group that is substituted with up to 3 alkyl groups.

Examples of triarylphosphines include $PPh_3$, triphenylphosphine, $P(C_6H_3Me_2)_3$, tris(dimethylphenyl)phosphine, $(C_6H_5)_2PC_6H_4CH_3$, diphenyl(p-tolyl)phosphine, diphenyl(o-tolyl)phosphine, (2-methylphenyl)diphenylphosphine, $P[(CH_3)_2C_6H_3]_3$, tris(3,5-dimethylphenyl) phosphine, tri-3,5-xylylphosphine, $(CH_3C_6H_4)_3P$, tris(o-tolyl)phosphine, $[(CH_3)_3C_6H_2]_3P$, tris(2,4,6-trimethylphenyl)phosphine, and trimesitylphosphine.

Under one embodiment the triaryl phosphine is triphenylphosphine.

The present invention is also directed to a powder composition for forming a cosmetic nail coating comprising (a) acrylic polymer or copolymer; and (b) about 0.01 wt % to about 1.0 wt % of a tertiary phosphine, wherein the tertiary phosphine comprises more than one phosphine atom. Examples of tertiary phosphines comprising more than one phosphine atom include 2,2'-bis(diphenylphosphino)-1,1'-biphenyl; 4,12-bis(diphenylphosphino)-[2.2]-paracyclophane; 4,12-bis[di(3,5-xylyl)phosphino]-[2.2]-paracyclophane; 1,4-bis(diphenylphosphino)butane; and mixtures thereof.

The compound 2,2'-bis(diphenylphosphino)-1,1'-biphenyl is a solid aryl phosphine of formula $Ph_2P—C_6H_4—C_6H_4—PPh_2$.

The compound 4,12-bis(diphenylphosphino)-[2.2]-paracyclophane is a solid aryl phosphine of formula $Ph_2P—C_6H_3[CH_2—CH_2]_2C_6H_3—PPh_2$. This compound may have the (S)-(+) configuration, or the (R)-(−) configuration, or a mixture thereof. The common names for these configurations are (S)-phanephos and (R)-phanephos, respectively.

The compound 4,12-bis[di(3,5-xylyl)phosphino]-[2.2]-paracyclophane is a solid aryl phosphine of formula $(C_6H_3Me_2)_2P—C_6H_3[CH_2—CH_2]_2C_6H_3—P(C_6H_3Me_2)_2$. This compound may have the (S)-(+) configuration, or the (R)-(−) configuration, or a mixture thereof. The common names for these configurations are (S)-xylyl-phanephos and (R)-xylyl-phanephos, respectively.

The compound 1,4-bis(diphenylphosphino)butane is a white solid tertiary phosphine of formula $Ph_2P—(CH_2)_4—PPh_2$. This compound is commonly abbreviated as $DPPh_2$.

The tertiary phosphine or the triaryl phosphine of the present invention not limited by any physical characteristic, as long as the use of the powder composition comprising the tertiary phosphine is easily flowable, and wets out to provide an even coating. Under one embodiment the even coating is a porous-free coating.

Under one embodiment, the tertiary phosphine is a solid. Such a solid is mixed into the acrylic polymer or copolymer until the resulting mixture is homogeneous. The mixing may be done via any viable mixing method. Generally, tertiary phosphines that are triaryl phosphines are solids.

Under another embodiment, the tertiary phosphine is a liquid. Such a liquid is mixed into the acrylic polymer or copolymer until the resulting mixture is homogeneous. The mixing may be done via any viable mixing method. Care must be used to assure that the resulting mixture of the powder acrylic polymer or copolymer with the liquid tertiary phosphine yields a powder that has an acceptable flow. An excipient, such as a flow modifier, may be added.

Under another embodiment the powder composition comprising acrylic polymer or copolymer and tertiary phosphine is formed during any of the steps of polymerization of the acrylic polymer or copolymer. The tertiary phosphine is added to the composition prior to the finalization of the polymerization of the acrylic polymer or copolymer. The resulting powder composition may yield a powder, wherein the core of the powder particles comprises acrylic polymer or copolymer, and the surface of the powder particles comprises tertiary phosphine adduct.

Under one embodiment of the present invention, the powder composition comprising the acrylic polymer or copolymer, and tertiary phosphine have an easy flow. An easy flow allows the powder composition to be easily placed into the contact with a cyanoacrylate adhesive. An easy flow also allows for the powder to wet out over the cyanoacrylate adhesive.

The classification of the flow of a powder can be quantified by the flow factor value or the failure function slope value. Powders in the de-aerated state can be classified on the basis of direct tests results using a shear cell tester of a compression tackiness tester. The shear cell tester measures different shearing forces for corresponding normal force on consolidated powder samples. For each yield locus the unconfined yield stress and major consolidation stress $\sigma_1$ (i.e., the maximum normal stress underwent by a certain powder at a given state of compaction) can be obtained. Unconfined yield stress f, is the normal stress necessary to make the powder yield at zero shear stress (i.e., no shear forces in the planes perpendicular to the normal force). The flow factor ff is the ratio of the major consolidated stress $\sigma_1$ found from the yield locus to the unconfined yield strength f, as represented by the formula $ff=\sigma_1/f_c$.

Under one embodiment of the present invention, the flow factor ff is more than about 4. Under another embodiment, the flow factor is more than about 6. Under yet another embodiment, the flow factor is more than about 8.

The flow factor may be ascertained from data obtained from any number of powder flow testers. Examples of powder flow testers include Brookfield PFT, Jenike shear cell, Shultze RST, and like.

The flow factor may be ascertained by using a validated laboratory method of measuring flowability. The laboratory method may be designed by the testing laboratory, or it may be a standard method. Suitable standard methods include ASTM D6128.

The powder composition for forming a cosmetic nail coating comprises polyethyl methacrylate polymer, and about 0.01 wt % to about 1.0 wt % of tertiary phosphine. Under one embodiment the powder of composition comprises about 0.03 wt % to about 0.50 wt % of triphenylphosphine. Under another embodiment, the powder of composition comprises about 0.05 wt % to about 0.25 wt % of triphenylphosphine.

The weight of the tertiary phosphine is measured with respect to the entire powder composition.

Under one embodiment, the powder composition for forming a cosmetic nail coating comprises only two components, namely, polyethyl methacrylate polymer; and a tertiary phosphine. Under an alternative embodiment, the powder composition further comprises one or more excipients. Examples of suitable excipients include flow modifiers and colorants.

The powder composition of the present invention under one embodiment comprises a small amount of a flow modifier. A flow modifier is a composition that aids in the flow of the powder composition. The flow modifier helps to decrease the apparent viscosity of the powder composition. The flow modifier increases the flow factor. The flow modifier increases the wetting action of the powder composition over the nail coated with a layer of a cyanoacrylate adhesive.

The powder composition of the present invention under one embodiment comprises a small amount of a colorant or special effects pigment or a combination thereof.

One purpose of using pigment in the powder composition is to provide a tint or a color to the formed cosmetic nail coating. The use of such color in the powder composition may allow the manicurist to omit certain selected post-treatment steps after the formation of the cosmetic nail coating.

Another purpose of using a pigment is to give a clear or colorless or whitish appearance of the cosmetic nail coating. The pigment may be used to address any yellowing of the cosmetic nail coating.

Yet another purpose of using a pigment is to provide a whitish appearance to the powder composition so that it appears as an attractive, clean product to the manicurist.

Examples of pigments may be incorporated into the powder composition of the present invention include: annatto, caramel, carmine, β-carotene, potassium sodium copper chlorophyllin (chlorophyllin copper-complex), dihydroxyacetone, bismuth oxychloride, guaiazulene, iron oxides, ferric ammonium ferrocyanide, ferric ferrocyanide, chromium hydroxide green, chromium oxide greens, guanine, pyrophyllite, mica, silver, titanium dioxide, aluminum powder, bronze powder, copper powder, ultramarines, manganese violet, zinc oxide, luminescent zinc sulfide, FD&C Blue No. 1, D&C Blue No. 4, Iron Blue, D&C Brown No. 1, FD&C Green No. 3, D&C Green No. 5, D&C Green No. 6, D&C Green No. 8, D&C Orange No. 4, D&C Orange No. 5, D&C Orange No. 10, D&C Orange No. 11, FD&C Red No. 4, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, FD&C Red No. 40, D&C Violet No. 2, Ext. D&C Violet No. 2, FD&C Yellow No. 5, FD&C Yellow No. 6, D&C Yellow No. 7, Ext. D&C Yellow No. 7, D&C Yellow No. 8, D&C Yellow No. 10, D&C Yellow No. 11, and mixture of any of the preceding. As will be recognized by the practitioner of the art, some of the pigments in the above list are better suited for use in the powder composition than others, because they offer better composition stability of the powder composition, and they do not interfere with the curing process.

Under one embodiment the photopolymerizable composition comprises the pigment is selected from the group consisting of ultramarine, manganese violet, zinc oxide, FD&C Blue No. 1, D&C Blue No. 4, Iron Blue, D&C Violet No. 2, and a mixture thereof.

Special effects pigment may be any pigment that gives either the powder composition or the formed cured composition a special effect, such as an increased pearlescent, iridescent, shimmering, transparency or a complex effects. Examples of special effect pigments include titanated micas, mica-based interference colors, mica coated with titanium dioxide and iron oxide, mica-based gold pearls, mica-based metallic pearls, mica-based pearl pigments, bismuth oxychloride, synthetic mica-based interference pearls, synthetic mica-based white pigment, silicate-based pearls, titanium oxide and tin oxide on silicate platelets, flaked aluminum powder, silver coated silicate flakes, and any combination of the foregoing.

Under one embodiment, the powder composition is shelf stable. For example, the powder composition is stable in a dark container at 20° C. for more than six months.

The term "stable" refers to the lack of change in the physical, chemical or esthetic properties of the powder composition that would make the powder composition unsuitable for sale to the consumer or would unsuitable for use by the manicurist. Exemplary changes of physical, chemical or esthetic properties of the powder composition include the decrease in the flow factor ff, noticeable yellowing of the powder, and noticeable decrease in the wetting action of the powder composition over a nail comprising a cyanoacrylate adhesive.

The present invention relates to a method of forming a cosmetic nail coating comprising the steps of (i) applying to a nail a cyanoacrylate adhesive; and (ii) contacting the nail with a powder composition comprising (a) acrylic polymer or copolymer; and (b) about 0.01 wt % to about 1.0 wt % of tertiary phosphine of formula $PAr_aR_{3-a}$, wherein each Ar is independently selected from the group consisting of $C_6H_5$, $C_6H_{5-n}R'_n$, $C_{10}H_7$, $C_{10}H_{7-n}R'_n$; a=0, 1, 2, or 3; n=0, 1, 2, or 3; each R is independently an alkyl group comprising 0 to 8 carbons; each R' is independently an alkyl group comprising 0 to 8 carbons; and wherein wt % is with respect to the powder composition.

This method comprises two steps. In the first step, the manicurist applies a layer of a cyanoacrylate adhesive. Immediately thereafter, the manicurist contacts the nail coated with the layer of the cyanoacrylate adhesive with a powder composition comprising the acrylic polymer or copolymer and tertiary phosphine. One possible description of the powder composition is described above.

These two steps may be repeated twice, thrice, or more times. Each repetition of the two-step method may be similar to other repetitions, or they may be somehow different. For example, the powder composition may be different for each repetition: once the powder may be white, and the next time it may have a colorant in the powder composition.

The term "contact" means any type of an application of the powder composition onto the cyanoacrylate adhesive that will permit the powder composition to react with the adhesive to form a nail coating composition. An example of contacting the powder to the nail comprising the cyanoacrylate adhesive includes dipping the finger into the powder and sprinkling the powder onto the finger.

The method of forming a cosmetic nail coating may be preceded by preparative steps. Such steps may include a wash of the client's hands, having the client wash her hands, removing any prior nail polish. The nails may be trimmed if needed and shape as desired with a file. The eponychium may be pushed back to reveal the true cuticle. Any residue may be removed with a nail wipe.

A dual-edge nail plate cleaner may be used to remove excess non-living tissue. Further, any hangnails and remaining non-living tissue may be removed with nippers.

The nail surface may be buffed with the 220-grit buffer. The resulting dust may be removed and nail cleansed with a nail wipe and the nail is allowed to dry.

A coat of pH balancing agent may be added to each nail, and the nails may be allowed to dry.

The method of forming a cosmetic nail coating may be followed by finishing steps. Once the method of forming a cosmetic nail coating is complete, any excess powder may be tapped off. When the cosmetic nail coating is dry to the touch, a sanitized cosmetic brush may be used to wipe off any remaining loose powder.

Under one embodiment of the present invention, an air-dry top coat is added to the nail and allowed to air dry. The air-dry top coat may be any air-dry top coat commonly available in the manicure industry. An exemplary air-dry top coat comprises ethyl acetate, butyl acetate, isopropyl alcohol, cellulose acetate butyrate, acetyl tributyl citrate, nitrocellulose, acrylates copolymer, phthalic anhydride/trimellitic anhydride/glycols copolymer, camphor, etrocrylene, and Violet 2.

The present invention relates to a method of forming a cosmetic nail coating comprising the steps of (i) applying to a nail a cyanoacrylate adhesive; and (ii) contacting the nail with a powder composition comprising acrylic polymer or copolymer and tertiary phosphine. Cyanoacrylate adhesives are well known in the nail industry. For example, cyanoacrylate adhesives are used in the traditional dip powder systems. Further, cyanoacrylate adhesives are used to adhere artificial nails to natural nails.

The cyanoacrylate adhesive as used in the above-described method may be a cyanoacrylate adhesive commercially available to nail salons. Alternatively, the cyanoacrylate adhesive may be an experimental cyanoacrylate adhesive.

The cyanoacrylate adhesive comprises a cyanoacrylate. The cyanoacrylate adhesive may further comprise an excipient. Examples of cyanoacrylate adhesive excipients include acidic inhibitors and polymers (such as PMMA).

Suitable cyanoacrylates include alkyl cyanoacrylates and alkoxy cyanoacrylates. Under one embodiment, for alkyl cyanoacrylates, the alkyl group(s) contains 1 to 10 carbon atoms. Under another embodiment, for alkyl cyanoacrylates, the alkyl group(s) contains 1 to 6 carbon atoms. Under yet another embodiment, for alkyl cyanoacrylates, the alkyl group(s) contains 1 to 4 carbon atoms.

Under one embodiment, for alkoxy cyanoacrylates, the alkoxy group(s) contains 1 to 5 carbon atoms. Under another embodiment, for alkoxy cyanoacrylates, the alkoxy group(s) contains 1 to 4 carbon atoms. Under yet one embodiment, for alkoxy cyanoacrylates, the alkoxy group(s) contains 1 to 3 carbon atoms.

Specific example of suitable cyanoacrylates include 2-ethyl cyanoacrylate, 2-cyanoacrylate, methyl 2-cyanoacrylate, n-propyl 2-cyanoacrylate, isopropyl 2-tert-butyl cyanoacrylate, 2-cyanoacrylate, n-butyl 2-cyanoacrylate, isobutyl 3-methoxybutyl cyanoacrylate, cyanoacrylate, n-decyl 2-cyanoacrylate, hexyl 2-cyanoacrylate, 2-ethoxyethyl 2-cyanoacrylate, 2-methoxyethyl 2-cyanoacrylate, 2-octyl 2-cyanoacrylate, 2-propoxyethyl 2-cyanoacrylate, n-octyl cyanoacrylate, isoamyl cyanoacrylate, and mixtures thereof.

Cyanoacrylates include those of the formula NC—C($=CH_2$)—CO—OZ, wherein: Z is selected from the group consisting of —$(CH_2)_7$—$CH_3$, —$CH(CH_3)$—$(CH_2)_5$—$CH_3$, —$CH_2$—$CH(C_2H_5)$—$(CH_2)_3$—$CH_3$, —$(CH_2)_5$—$CH(CH_3)$—$CH_3$, —$(CH_2)_4$—$CH(C_2H_5)$—$CH_3$.

Under one embodiment the cyanoacrylate adhesive comprises a reactive cyanoacrylate composition selected from the group consisting of methyl 2-cyanoacrylate, ethyl 2-cyanoacrylate, n-butyl cyanoacrylate, 2-octyl cyanoacrylate, and a mixture thereof.

The present invention relates to a nail coating composition formed by the above-described method.

The nail coating composition under one embodiment is the layered mixture of cyanoacrylate adhesive and the powder composition, at the time prior to the curing of the nail coating composition. Under an alternative embodiment, the nail coating composition is the layered mixture of cyanoacrylate adhesive and the powder composition, at the time after the curing of the nail coating composition. Under yet another embodiment, the nail coating composition is the layered mixture of cyanoacrylate adhesive and the powder composition, at any time, including before and after the curing of the nail coating composition.

Under one embodiment, the curing may be aided by applying an activator after contacting of the powder composition with the cyanoacrylate adhesive. The activator comprises a solvent, such as ethyl acetate, butyl acetate, isopropyl acetate, or a mixture thereof, and a tertiary amine.

Under an alternative embodiment, the nail coating composition formed by the method of applying the cyanoacrylate adhesive and powder composition is fully cured without the need for the activator. Specifically, the present invention is directed to a cured nail coating composition formed by (i) applying to a nail a cyanoacrylate adhesive; and (ii) contacting the nail with a powder composition comprising (a) acrylic polymer or copolymer; and (b) about 0.01 wt % to about 1.0 wt % of tertiary phosphine, wherein the cured nail composition is cured only by the reaction of the cyanoacrylate adhesive, the acrylic polymer or copolymer, and the tertiary phosphine.

Under one embodiment of the present invention, the cure time is less than about 1 minute. Under an alternative embodiment, the cure time is less than about 40 seconds.

One of the advantages of the present invention is that the use of tertiary phosphine mitigates yellowing, compared to the yellowing exhibited by dip powder systems that are cured with the aid of an activator. One aspect of the present invention is also directed to the cured nail composition, wherein the yellowness index of the cured nail composition is less than the yellowness index for the equivalent formulation comprising tertiary amine instead of tertiary phosphine.

Under this aspect, the yellowness index of the dip powder system that is cured by the aid of tertiary phosphine is of a lower value than a comparable dip powder system that is cured by the aid of a tertiary amine.

EXAMPLES

A series of nine formulations of powder polymer mixtures were tested. Three formulations (Examples 1, 2, and 3) contained either BPO or no accelerators; three formulations (Examples 4, 5, and 6) comprised a tertiary amine accelerator DHEPT; and three formulations (Examples 7, 8, and 9) comprised a tertiary phosphine accelerator TPP.

| Chemical name | 1 | 2 | 3 | 4 | 5 | 6 | 7 | 8 | 9 |
|---|---|---|---|---|---|---|---|---|---|
| Powder polymer | 100 | 89.4 | 78.7 | 93.2 | 96.6 | 98.7 | 99.3 | 99.6 | 99.9 |
| PEMA/PMMA copolymer | | 9.8 | 19.2 | | | | | | |
| BPO | | 0.8 | 2.1 | | | | | | |
| DHEPT | | | | 6.8 | 3.4 | 1.4 | | | |
| TPP | | | | | | | 0.69 | 0.25 | 0.06 |
| Silica | | 0.03 | 0.01 | | | | | 0.2 | |
| Average Cure Time | 2:21 | 1:53 | 1:53 | 2:18 | 3:19 | 8:18 | 0:35 | 0:38 | 1:04 |

For each of the formulations, the above ingredients were added together and mixed until the composition was homogeneous. The order of addition of the ingredients did not show any appreciable differences in the performance of the composition.

The procedure for testing the cure time for the above formulations comprising either BPO or no accelerators (i.e., formulations of Examples 1 to 3) were as follows:
(1) apply a layer of a resin to a model nail;
(2) dip the model nail into the powder polymer mixture;
(3) shake off any excess powder polymer mixture;
(4) apply another layer of the resin to a model nail;
(5) dip the model nail into the powder polymer mixture again;
(6) shake off any excess powder polymer mixture; and
(7) apply a layer of an activator.

The procedure for testing the cure time for the formulations comprising the tertiary amine or tertiary phosphine accelerators (i.e., formulations of Examples 4 to 9) were the same as above, except step (7) was omitted.

In addition to the nine examples above, the formulation of Example 1 was repeated, except that step (7) omitted. The cure time for this example (i.e., without either an application of an activator layer or inclusion of an accelerator) is over 2 hours.

Each of the steps of this procedure approximated the method that a typical, well-trained manicurist would perform in a salon. The thickness of the layer of glue, the length of time that the model nail was placed into the powder polymer mixture, and other parameters, were selected to be about the same as those used in salons.

The above procedure was repeated for each of the formulations. The repetitions showed that the cure time is highly reproducible. The mean cure time for each formulation is also listed in the above table.

The analysis of the above data showed, firstly, that either the inclusion of an accelerator in the powder or an application of an activator layer is needed for the cure time to be commercially viable. Secondly, the data shows that either the use of a tertiary amine or triphenylphosphine helps to cure the nail coating. Thirdly, the data shows that the loading levels of the accelerator has a positive impact on shortening the length of the cure time. Fourthly, the data shows that the use of triphenylphosphine, even at relatively low loading levels, yields a short cure time.

The relationship between the loading level of triphenylphosphine and the average cure time was investigated.

| Exp No. | Wt % | t (sec) | 1/(wt %) | 1/t |
|---|---|---|---|---|
| 7 | 0.69 | 35 | 1.449 | 0.0286 |
| 8 | 0.25 | 38 | 4.000 | 0.0263 |
| 9 | 0.06 | 64 | 16.667 | 0.0156 |

A regression analysis shows that this data follows the equation:

$$1/t = -0.0008/(wt\%) + 0.0298$$

with $R^2 = 0.999$.

Further, it has been observed that model nails treated by the above method for formulations of Examples Nos. 4, 5, and 6 (wherein the powder comprises DHEPT) resulted in a nail coating that exhibited a slight yellowish tinge. The model nails treated by the above method for formulations of Examples Nos. 7, 8, and 9 (wherein the powder comprises TPP) resulted in a nail coating that did not exhibit any yellowish tinge.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. A powder composition for forming a cosmetic nail coating comprising:
   (a) acrylic polymer or copolymer; and
   (b) about 0.01 wt % to about 1.0 wt % of tertiary phosphine of formula $PAr_aR_{3-a}$, wherein each Ar is independently selected from the group consisting of $C_6H_5$, $C_6H_{5-n}R'_n$, $C_{10}H_7$, and $C_{10}H_{7-n}R'_n$,
   a=0 to 3;
   n=0 to 3;
   each R is independently an alkyl group comprising 1 to 8 carbons;
   each R' is independently an alkyl group comprising 1 to 8 carbons; and wherein all wt % are with respect to the powder composition.

2. The powder composition of claim 1, wherein the acrylic polymer or copolymer is selected from the group consisting of polymethyl methacrylate, polyethyl methacrylate, polybutyl methacrylate, or copolymers thereof.

3. The powder composition of claim 1, wherein the tertiary phosphine is a triaryl phosphine of formula $PAr_3$.

4. The powder composition of claim 3, wherein each Ar is independently $C_6H_5$ or $C_6H_{5-n}R'_n$.

5. The powder composition of claim 1, wherein the tertiary phosphine is triphenylphosphine.

6. The powder of composition of claim 1, wherein the powder composition comprises about 0.03 wt % to about 0.50 wt % of triphenylphosphine.

7. The powder of composition of claim 1, wherein the powder composition comprises about 0.05 wt % to about 0.25 wt % of triphenylphosphine.

8. The powder composition of claim 1, further comprising an excipient selected from the group consisting of a flow modifier and a colorant.

9. The powder composition of claim 1, wherein the powder composition is stable in a dark container at 20° C. for more than six months.

10. The powder composition of claim 1, wherein the powder composition's flow factor value as measured by ASTM D6128 is more than about 4.

11. A powder composition for forming a cosmetic nail coating comprising:
    (a) acrylic polymer or copolymer; and
    (b) about 0.01 wt % to about 1.0 wt % of a tertiary phosphine selected from the group consisting of 2,2'-bis(diphenylphosphino)-1,1'-biphenyl; 4,12-bis(diphenylphosphino)-[2.2]-paracyclophane; 4,12-bis[di(3,5-xylyl)phosphino]-[2.2]-paracyclophane; 1,4-bis(diphenylphosphino)butane; and mixtures thereof.

12. A method of forming a cosmetic nail coating comprising the steps of
    (i) applying to a nail a cyanoacrylate adhesive; and
    (ii) contacting the nail with a powder composition comprising (a) acrylic polymer or copolymer; and (b) about 0.01 wt % to about 1.0 wt % of tertiary phosphine of formula $PAr_aR_{3-a}$, wherein each Ar is independently selected from the group consisting of $C_6H_5$, $C_6H_{5-n}R'_n$, $C_{10}H_7$, $C_{10}H_{7-n}R'_n$; a=0, 1, 2, or 3; n=0, 1, 2, or 3; each R is independently an alkyl group comprising 1 to 8 carbons; each R' is independently an alkyl group comprising 1 to 8 carbons; and wherein wt % is with respect to the powder composition.

13. The method of claim 12, wherein the cyanoacrylate adhesive comprises a reactive cyanoacrylate composition selected from the group consisting of methyl 2-cyanoacrylate, ethyl 2-cyanoacrylate, n-butyl cyanoacrylate, 2-octyl cyanoacrylate, and a mixture thereof.

14. The method of claim 12, wherein the acrylic polymer or copolymer is selected from the group consisting of polymethyl methacrylate, polyethyl methacrylate, polybutyl methacrylate, or copolymers thereof.

15. The method of claim 12, wherein the tertiary phosphine is triphenylphosphine.

16. A nail coating composition formed by the method of claim 12.

17. A cured nail coating composition formed by the method of claim 12, wherein the cured nail composition is cured only by the reaction of the cyanoacrylate adhesive, the acrylic polymer or copolymer, and the tertiary phosphine.

18. The cured nail composition of claim 17, wherein the cure time is less than about 1 minute.

19. The cured nail composition of claim 17, wherein the cure time is less than about 40 seconds.

20. The cured nail composition of claim 17, wherein the yellowness index of the cured nail composition is less than the yellowness index for the equivalent formulation comprising tertiary amine instead of tertiary phosphine.

21. The cured nail composition of claim 17, further comprising an air-dry top coat.

* * * * *